(12) United States Patent
Siddiqui

(10) Patent No.: US 10,454,980 B1
(45) Date of Patent: Oct. 22, 2019

(54) REAL-TIME MEETING ATTENDANCE REPORTING

(71) Applicant: Amazon Technologies, Inc., Seattle, WA (US)

(72) Inventor: Ahmed Fuad Siddiqui, Everett, WA (US)

(73) Assignee: Amazon Technologies, Inc., Seattle, WA (US)

( * ) Notice: Subject to any disclaimer, the term of this patent is extended or adjusted under 35 U.S.C. 154(b) by 263 days.

(21) Appl. No.: 15/663,017

(22) Filed: Jul. 28, 2017

Related U.S. Application Data

(63) Continuation of application No. 13/858,847, filed on Apr. 8, 2013, now Pat. No. 9,723,035.

(51) Int. Cl.
| | |
|---|---|
| *G06F 3/048* | (2013.01) |
| *H04L 29/06* | (2006.01) |
| *G16H 40/20* | (2018.01) |
| *G06F 16/2457* | (2019.01) |

(52) U.S. Cl.
CPC ...... *H04L 65/403* (2013.01); *G06F 16/24573* (2019.01); *G16H 40/20* (2018.01)

(58) Field of Classification Search
CPC .. H04L 65/403; G16H 40/20; G06F 16/24573
USPC ........................................................ 715/753
See application file for complete search history.

(56) References Cited

U.S. PATENT DOCUMENTS

| | | | |
|---|---|---|---|
| 6,480,830 B1 | 11/2002 | Ford et al. | |
| 7,036,128 B1 | 4/2006 | Julia et al. | |
| 7,231,423 B1 | 6/2007 | Horstmann et al. | |
| 7,620,902 B2 | 11/2009 | Manion et al. | |
| 7,721,224 B2 | 5/2010 | Sellen et al. | |
| 8,161,069 B1 | 4/2012 | Wilder et al. | |
| 8,260,321 B1 | 9/2012 | Dunko | |
| 8,359,538 B2 | 1/2013 | Jyrinki | |
| 8,478,622 B2 | 7/2013 | Grodum | |
| 8,577,974 B2 | 11/2013 | Paulsami et al. | |
| 8,612,876 B2 | 12/2013 | Barnett et al. | |
| 8,688,779 B2 | 4/2014 | Bocking et al. | |
| 8,717,407 B2 | 5/2014 | Kulkarni et al. | |
| 8,719,717 B2 | 5/2014 | Kalu | |
| 9,021,034 B2* | 4/2015 | Narayanan ........... G06Q 10/109 705/319 |
| 9,204,257 B1* | 12/2015 | Mendelson ............. G08G 1/14 |
| 9,436,934 B2* | 9/2016 | Bisht .................... G06Q 10/109 |

(Continued)

OTHER PUBLICATIONS

Office Action for U.S. Appl. No. 13/858,847, dated Jan. 5, 2015, Ahmed Fuad Siddiqui, "Real-Time Meeting Attendance Reporting", 4 pages.

(Continued)

*Primary Examiner* — David Phantana-angkool
(74) *Attorney, Agent, or Firm* — Lee & Hayes, P.C.

(57) ABSTRACT

Techniques are described for creating real-time reports of meeting attendance. A calendar is accessed to determine the scheduled time and participants of a meeting. During the scheduled time of the meeting, locations of the scheduled participants are determined by obtaining position information from mobile devices carried by the participants. A meeting report is generated for any one or more of the participants, listing those participants who are present at the meeting. Relative positions of the attending participants may also be shown.

20 Claims, 4 Drawing Sheets

(56) References Cited

U.S. PATENT DOCUMENTS

| | | | |
|---|---|---|---|
| 9,723,035 B1* | 8/2017 | Siddiqui | H04L 65/403 |
| 9,824,333 B2* | 11/2017 | Shaw | G06Q 10/109 |
| 9,967,705 B2* | 5/2018 | Trivedi | H04W 4/021 |
| 2007/0226034 A1 | 9/2007 | Khan | |
| 2009/0148827 A1 | 6/2009 | Argott | |
| 2011/0271206 A1 | 11/2011 | Jones et al. | |
| 2013/0298037 A1 | 11/2013 | Matthews, III et al. | |
| 2014/0157166 A1 | 6/2014 | Choi | |

OTHER PUBLICATIONS

Office action for U.S. Appl. No. 13/858,847 dated Nov. 17, 2015, Siddiqui, "Real-Time Meeting Attendance Reporting", 9 pages.

* cited by examiner

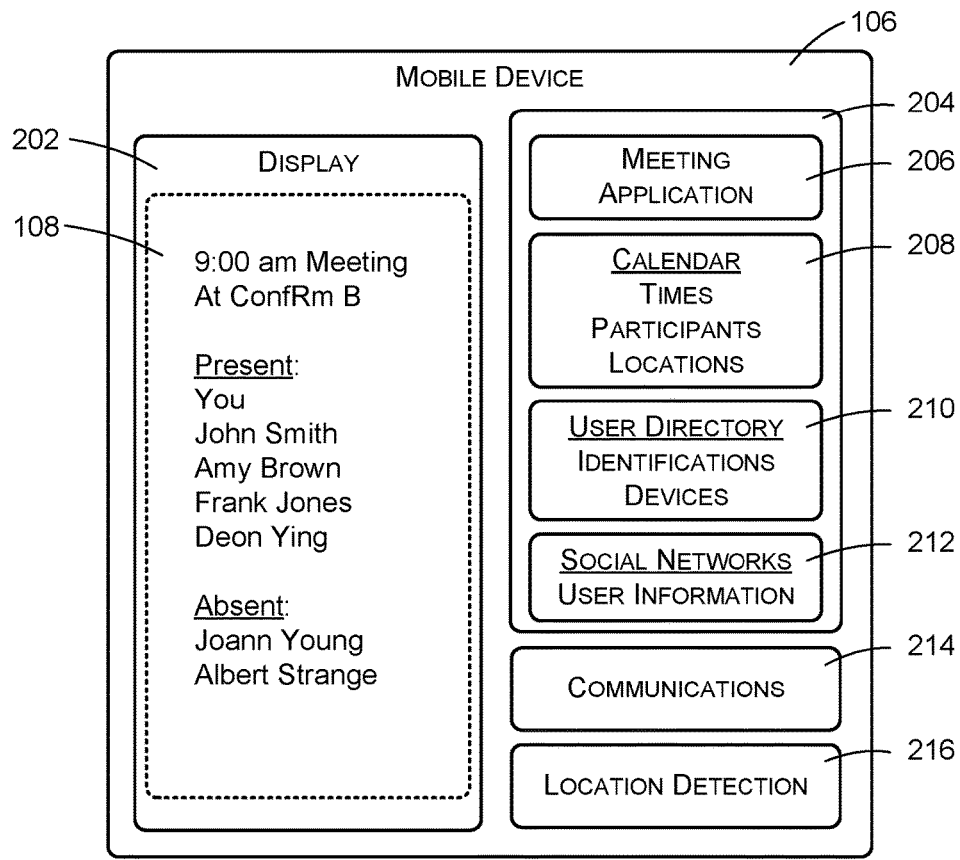
FIG. 2
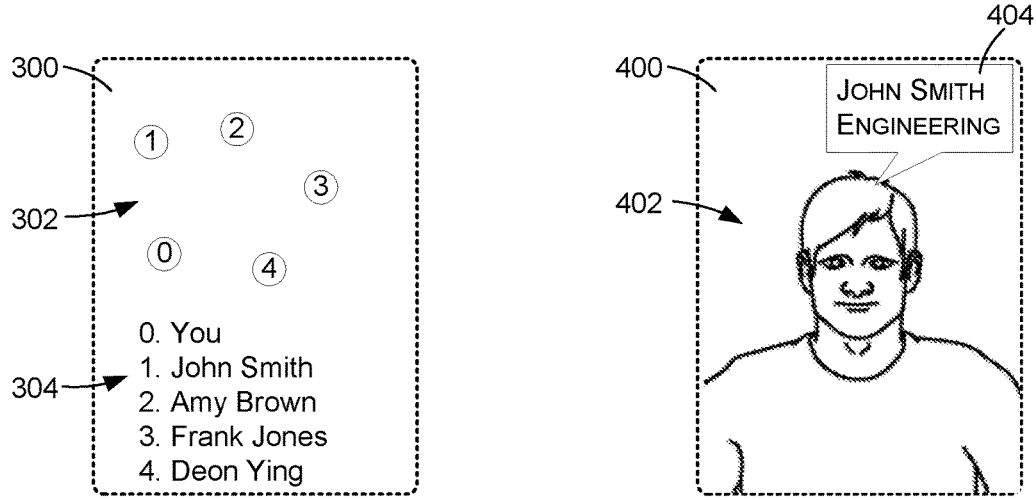
FIG. 3
FIG. 4

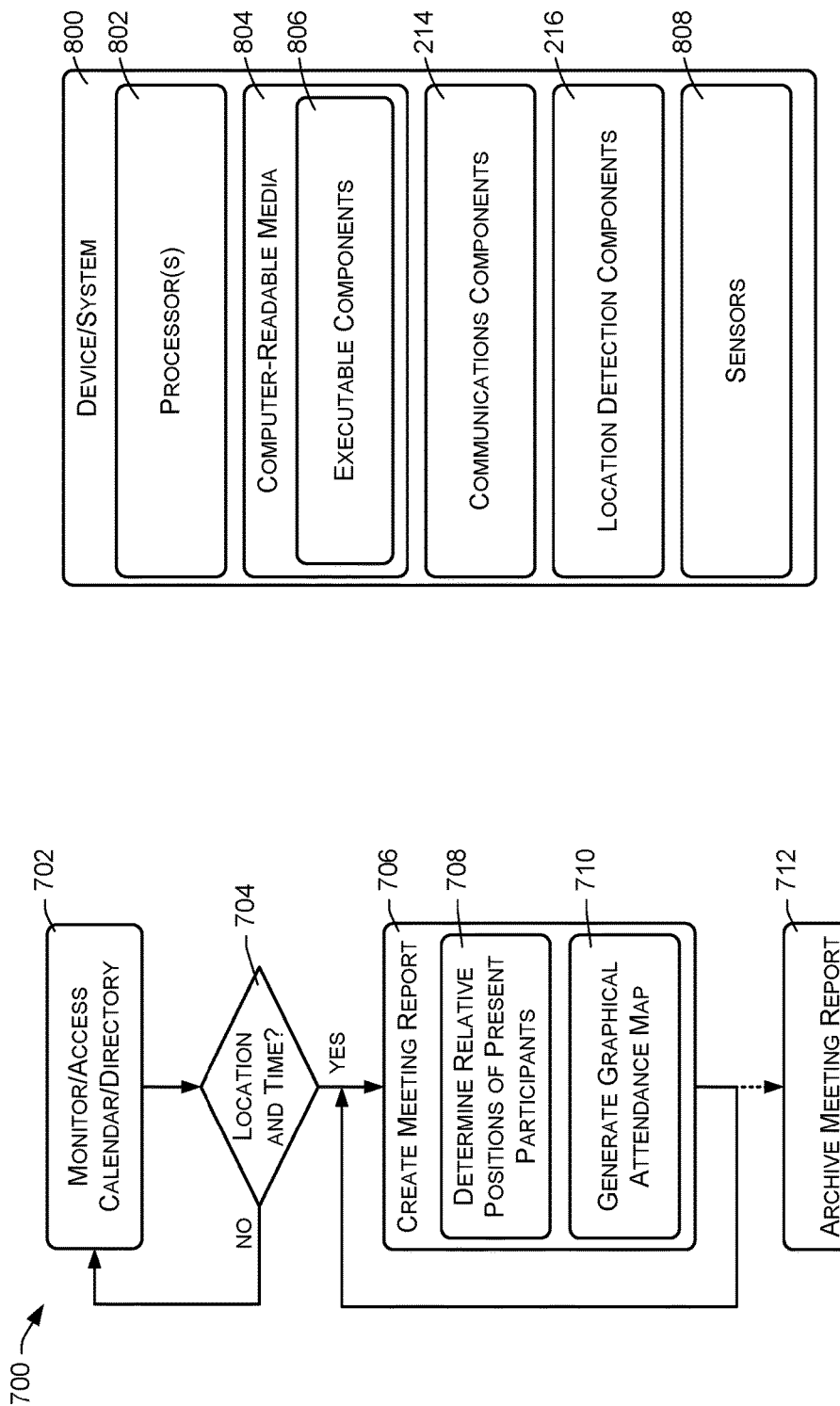

REAL-TIME MEETING ATTENDANCE REPORTING

CROSS REFERENCE TO RELATED APPLICATIONS

This application is a continuation of co-pending U.S. application Ser. No. 13/858,847 filed Apr. 8, 2013 entitled "Real-Time Meeting Attendance Reporting," which is incorporated herein by reference in its entirety.

BACKGROUND

Personal mobile devices such as smartphones have become so common that most people carry one with them at all times. Modern smartphones have a multitude of sensors, and are often capable of detecting device location, orientation, and motion. In addition, smartphones typically have various data communications capabilities, allowing them to reliably communicate with other devices as well as with servers and services.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

FIG. 2 is a block diagram illustrating functional components of a mobile device or other system that may be used to generate a real-time meeting report.

FIGS. 3-5 are examples of examples of meeting reports that may be generated and displayed to show attendance at scheduled meetings by participants.

FIG. 7 is a flow diagram illustrating generation of a real-time meeting report based on locations of scheduled meeting participants.

FIG. 8 is a block diagram of a mobile device that may be configured to implement the techniques described herein.

DETAILED DESCRIPTION

This disclosure describes systems and techniques for reporting attendance at meetings as the meetings are conducted, using the capabilities of mobile devices that are carried by attendees and/or other scheduled participants of the meetings. A personal mobile device of a user may be configured to receive or determine the locations of mobile devices associated with other scheduled participants of a meeting. During a meeting, a user may view a meeting attendance report that lists the scheduled participants who are actually at the meeting, based on reported or determined locations of the mobile devices of the participants. In some embodiments, the mobile device of a user may generate a graphical attendance map, showing positions of attending participants in relation to the user. In some embodiments, the user may point their mobile device at other meeting participants, and the mobile device may identify the participants at which the device is pointed. The mobile device may also show selected information about other participants, such as information obtained from contact lists and/or social networking services.

Figure 1:
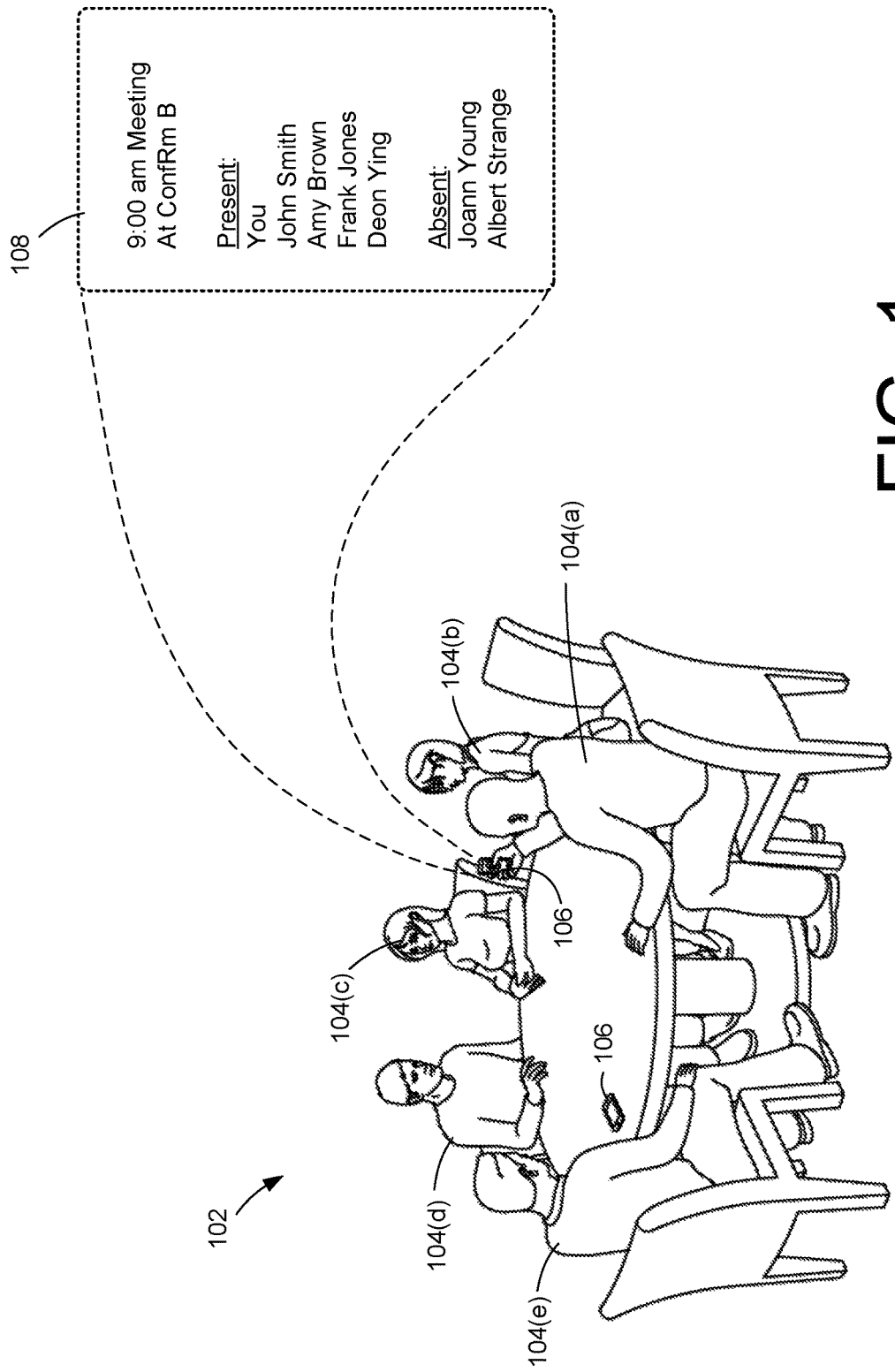
FIG. 1 illustrates a meeting environment and an example of a real-time meeting report that may be generated to view attendance of scheduled meeting participants.

FIG. 1 illustrates an example meeting location 102 at which several of multiple scheduled meeting participants 104(a)-104(e) (referred to collectively as participants 104) are present. Each of the scheduled participants 104 carries or has a personal mobile device 106. The mobile devices 106 associated with the participants 104(a) and 104(b) are shown in FIG. 1, while the mobile devices of other meeting participants may be out of view, such as within pockets, briefcases, or bags. Examples of personal mobile devices include smartphones, tablet computers, media players, and other portable devices that may be carried by and associated with a user.

Each of the personal mobile devices 106 is capable of generating and/or receiving position information that indicates whether the user of the mobile device is at the meeting location 102, and whether other scheduled participants are at the meeting location 102. In addition, the position information may in some embodiments indicate positions of the attending participants relative to each other and/or to the meeting location 102.

An individual user, such as the user 102(a), can view their mobile device 106 to see a meeting display or report 108, indicating which of the scheduled meeting participants are present at the meeting location. In the example of FIG. 1, the meeting report 108 shows information that identifies the meeting, such as the name, time, and location of the meeting, the names of scheduled participants who are present at the meeting location, and the names of scheduled participants who are absent from the meeting location FIG. 2 shows relevant functional elements of an example mobile device 106 that is configured to generate and/or receive position information, as well as to display meeting participant information to a user of the device 106. The mobile device 106 is also configured to work in conjunction with other mobile devices to allow such other mobile devices to display similar meeting participant information and meeting reports.

The mobile device 106 may include a graphical display 202 for presenting graphical information to the user of the mobile device 106. The graphical information may include the meeting report 108, which contains information relating to a scheduled meeting and to scheduled participants of the meeting. The mobile device 106 may also include one or more executable and/or data components 204 that operate in conjunction with each other to generate the meeting report 108 and to provide location or position information regarding the mobile devices of other meeting participants.

The executable components 204 may include a meeting application 206 that is configured to obtain information regarding meetings and the locations of scheduled meeting participants, and to display the meeting report 108 on the graphical display 202. The meeting application 206 may obtain or receive meeting information from a calendar or scheduling component 208. The calendar component 208 may be an application running on the mobile device 106, and may contain or reference a database indicating meetings that the user of the mobile device 106 is scheduled to attend. In addition, the calendar component 208 may indicate the time of each meeting and the participants who are scheduled to attend each meeting. In some embodiments, the calendar component 208 may indicate a location of the meeting. The location of a meeting, if indicated, may be specified in terms of position or geographic information, such as by position coordinates.

In some situations, the calendar component 208 may comprise an external application, server, or service that is accessible to the meeting application 206, such as a service that is accessible using Internet, networking, or web service technologies. For example, the calendar component 208 may comprise a centralized server or service to which all of the scheduled meeting participants subscribe.

The meeting application 206 may obtain or receive user or participant information from a user directory 210. The user directory 210 may indicate identifiers for various users and may also identify devices associated with the users. More specifically, the user directory 210 may provide a mapping between potential meeting participants and the mobile devices associated with such potential meeting participants. In some cases, the user directory 210 may comprise an application or database that is resident on the mobile device 106. Alternatively, the user directory 210 may comprise a network-based server, service, or database that is accessible to the meeting application 206 for obtaining user information. In a specific implementation, the user directory 210 may comprise a domain controller or associated local domain service that is used in conjunction with a local network of an organization.

The meeting application 206 may also obtain information regarding potential meeting participants from one or more social network components 212. Information available from online social networks may include contact information, photographs, biographies, resumes, email addresses, online user names, and so forth. The social network components 212 may comprise local applications or databases, which may in turn reference various types of network-based databases or services. Alternatively, the social network components 212 may comprise remote or network-based servers or services that are accessible to the meeting application 206.

The mobile device 106 may include other components that are used by or in conjunction with the meeting application 206 to generate the information presented by the meeting report 108. The other components may include communications components 214 that provide data communications with other mobile devices and/or remote servers, services, or applications. The communications components 214 may include any one or more of a wireless networking component, a cellular communications component, an RFID (radio-frequency identification) component, a near-field communications (NFC) component, a Bluetooth™ component, and other types of communications components. The communications components 214 may provide peer-to-peer communications with other mobile devices, and/or may provide broadcast or networked communications through various types of communications media, including wide-area networks, local-area networks, cellular networks, and so forth. In many embodiments, the communications components 214 may allow communications with other devices and remote services over the Internet and/or over other public and private networks.

The mobile device 106 may also have one or more location detection components 216 that provide position information regarding the mobile device 106 and/or other mobile devices that are associated with other scheduled meeting participants. Generally, the location detection components 216 are capable of determining (a) whether the mobile device 106 is at a meeting location and (b) whether the mobile devices of other scheduled meeting participants are at the meeting location. Thus, the location detection components 216 may determine or receive information about both the location of the mobile device 106 and the locations of other mobile devices. In certain embodiments, as will be described in more detail below, the location detection components may be capable of determining positions of the various mobile devices of meeting participants relative to each other and/or to a scheduled meeting location.

In some embodiments, each of the mobile devices of the scheduled meeting participants may be configured to determine its own location and to share that location with the mobile devices of the other scheduled participants. Position information may comprise absolute global coordinates of the mobile devices, such as may be obtained through the use of a global positioning system (GPS) or similar coordinate-based positioning system. Position information may alternatively indicate local coordinates relative to a limited area, such as relative to a room, building or campus. Various types of indoor or local-area positioning systems may be used for this purpose, and supported by the location detection components 216.

Position information may be provided or derived by other means, such as by estimating or triangulating the position of a mobile device based on various types of received signals, including cellular signals, wireless access point signals, positioning beacons, and so forth. As another example, near-field communications (NFC) tags and/or radio-frequency identification (RFID) devices may be placed at various locations within a meeting location, such as at various seating positions around a conference table, and the location detection components 216 may be configured to detect presence and/or location based on proximity to the tags or devices and on information received from the tags or devices. Other types of proximity detection technologies may alternatively be used to detect presence and/or location of a mobile device at a meeting location, or proximity of other mobile devices to a particular mobile device.

In some implementations, the mobile devices associated with multiple scheduled participants may be configured to interact with each other to determine inter-device positions and/or proximities. For example, Bluetooth™, NFC, and/or other wireless technologies may be used to determine relative proximities and/or positions of users. Various sensors of the mobile devices may also be used for determining relative positions of mobile devices, including motion sensors, gyroscopes, accelerometers, compasses, and so forth.

The location detection components 216 may be configured to communicate information regarding the location of the mobile device 106 with other mobile devices, and may additionally receive, generate, calculate, or estimate position information indicating the locations of such other mobile devices. Communications between devices may be through peer-to-peer communications mechanisms such as Bluetooth™ or through broadcast communications methods such as network communications. In some embodiments, inter-device communications may be facilitated by a central server or service, which may be accessible to each of the mobile devices over a network such as the Internet.

In operation, the meeting application 206 may be configured to monitor the calendar component 208 to determine times, locations, and scheduled participants of scheduled meetings. At or during the time of a meeting, the meeting application 206 may determine whether the user of the mobile device 106 is present at a meeting location, based on the location of the mobile device 106 of the user or on receiving an explicit indication from the user that the user has arrived at the meeting location. In addition, the meeting application 206 may determine whether other scheduled participants are present, based on position information that is generated or received regarding the positions of the mobile devices of the other participants. The meeting application 206 may determine that scheduled participants are present based on proximity of the mobile devices of such participants to each other. Alternatively, the meeting application may determine that scheduled participants are present based on detected positions of the associated mobile devices at a scheduled location of the meeting.

The meeting application 206 uses the determined presence information to generate the meeting report 108, which may list meeting information and attendance information. In the example shown in FIGS. 1 and 2, the meeting report 108 lists the time and location of the meeting, those of the scheduled participants who are present at the meeting location, and those of the scheduled participants who are absent from the meeting location.

Although certain techniques are described above as being implemented primarily by applications executing on mobile devices of respective users, much of the functionality described herein may be provided and performed by centralized servers or services, such as web servers. For example, the meeting report 108 may be generated and provided by a web server, based on information received from mobile devices of meeting participants. Each of the mobile devices may receive the meeting report 108 from such a web server and may display the meeting report using a generic content viewer such as a web browser.

FIG. 3 shows an example of an alternative meeting report 300, which may be generated during a meeting as described above to indicate attendance by scheduled participants of the meeting. In addition to listing those of the scheduled meeting participants who are actually present at the meeting, the report 300 shows a two-dimensional attendance map of an area that includes the attending participants, indicating the actual positions of the attending meeting participants relative to each other. In this example, each participant is represented by one of a plurality of numbered circular icons 302, and an index 304 lists the names of the participants represented by the icons. In other embodiments, participant names may be shown as direct annotations to the icons. In yet other embodiments, the icons may be replaced or supplemented by pictures of the participants, such as by pictures obtained from user directories, social networks, or other sources.

FIG. 4 shows another example of a meeting report 400. This example assumes that the user has pointed their mobile device 106 at one of the other meeting participants, as if taking a photograph or video of the other participant. A live or real-time video or moving image 402 of the other participant is shown on the graphical display 202 of the mobile device 106, as captured from a camera of the mobile device 106. An annotation 404 is generated and shown on the display 202, indicating the name of the meeting participant. The annotation 404 may include further information about the participant, such as the participant's title, organizational affiliation, or other details, including information that may be gleaned from online social networks, user directories, and so forth. As the user points the mobile device 106 in different directions, different participants may be shown in real time on the display 202, and the images may be annotated to identify any participants that are shown on the display 202.

The identity of the other participant at which the mobile device 106 is pointing may be ascertained by knowledge of the position of the other participant, obtained as described above, and by determining the position and orientation of the mobile device 106 using various sensors of the mobile device 106 such as compasses, gyroscopes, accelerometers, positioning elements, etc. Other techniques may also be used to identify pictured users, such as facial recognition techniques.

The various types of meeting reports described above may be used to display live or real-time information during the scheduled time of a meeting. The information may be provided to attendees of the meeting, as well as to non-attendees. In some cases, attendance for particular meetings may be recorded and archived based on the information obtained as described above.

Figure 5:
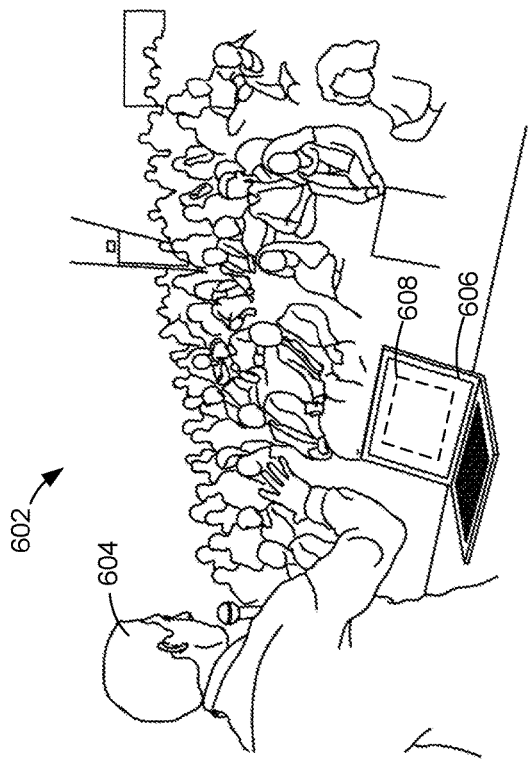

FIG. 5 shows an example of a meeting report 500 that may be generated and provided for viewing by a remote attendee or participant of a meeting as the meeting proceeds. In this example, the remote participant may be participating in the meeting by video conferencing, and the meeting report 500 may comprise a live video stream or image of physical attendees of the meeting. Based on the positions of the physical attendees, gathered as described above, a plurality of annotations 502 may be added to or superimposed on the live video image to show the names of the physical attendees. The meeting report 500 may be shown using videoconferencing equipment, on a personal computer of the remote attendee, or on a mobile device of the remote attendee.

Figure 6:
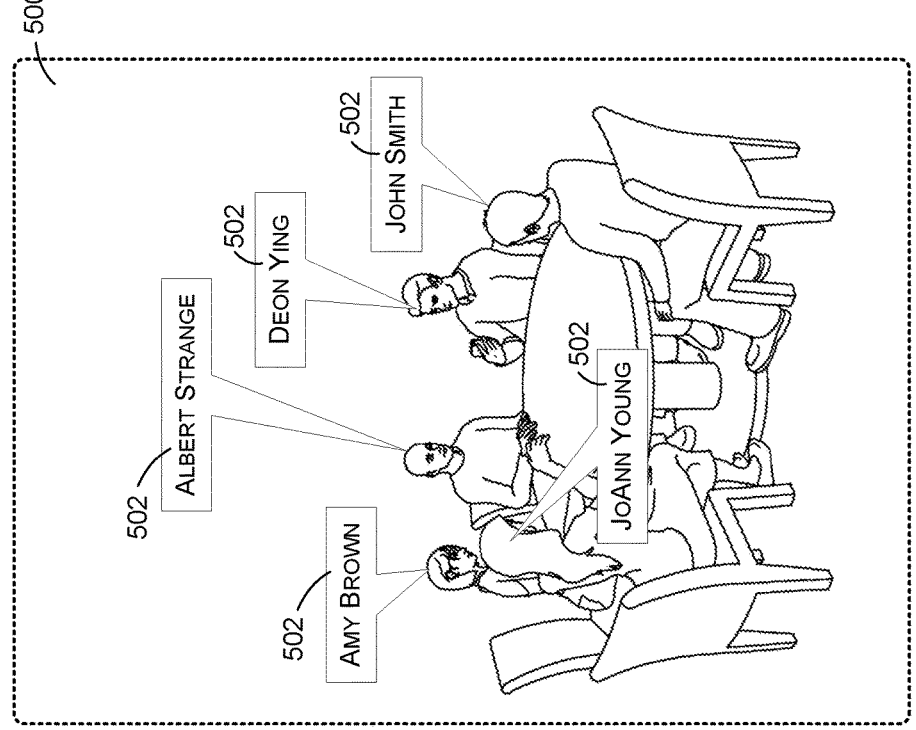
FIG. 6 illustrates a meeting environment in which the techniques described herein may be employed.

FIG. 6 shows an example in which the meeting attendance reporting techniques described above are used in a setting that includes a larger number of participants, such as participants 602 of a meeting in a hall, stadium, or auditorium. In this situation, a meeting leader or moderator 604 may make a presentation to the participants 602. The moderator 604 may have a personal computer or other device having a graphical display 606, upon which may be presented a graphical map 608 of the auditorium and the positions of individual meeting participants relative to each other and to the auditorium. The map may identify each of the meeting participants by name.

In this example, it is assumed that each of the participants 602 carries a mobile communications device to facilitate positional detection. As an example, each of the mobile communications devices may report its location to a central server or service, which may then generate a seating map on the display 606 for reference by the moderator. As another example, local groups of devices may interact to form local device maps, indicating the positions of the mobile devices within each group. The local maps may subsequently be combined by a server or service to produce a larger map that indicates positions of all participants who are present.

In situations like this that include a meeting leader or moderator, the leader or moderator may reference an attendance map or report when calling upon individual participants of the meeting. More specifically, the attendance map may list attending meeting participants, and may allow the moderator to select individual participants who wish to speak. In response to selecting or authorizing one of the participants, audio from a microphone of that participant's mobile device may be captured or received, and reproduced on a sound system of the meeting location so that the selected participant may speak to all of the participants. In some cases, video from the front- or rear-facing video camera of the selected participant's mobile device may also be received and displayed on a presentation system within the meeting location.

In alternative embodiments, an attendance list may be generated for the meeting leader or moderator based on explicit requests or check-ins by meeting participants. For example, a participant who wants to speak may use an application of his or her mobile device to register for the meeting and/or to submit a request to speak. The request may be queued, and the queued requests may be presented as part of a graphical interface to the meeting leader. At an appropriate time, the meeting leader may select one of the queued participants who has requested an opportunity to speak. In response, the microphone and/or front- or rear-facing video camera of the participant's mobile device may be activated and/or enabled, so that spoken audio and video of the participant may be received and reproduced using multimedia presentation capabilities of the meeting location, such as sound systems and video projection systems.

FIG. 7 illustrates an example method 700 of automatically creating and presenting real-time meeting attendance reports for meeting attendees and others. The example method may be performed in the various contexts described above, as well as in other situations that have not been specifically described.

An action 702 comprises accessing and/or monitoring a calendar to determine a time of a meeting and to identify one or more scheduled participants of the meeting. In some embodiments, the action 702 may also include identifying a location of the meeting. A meeting location may be specified using global or local geographic coordinates. Alternatively, a meeting location may be specified or characterized in terms of different types of detectable signals that may be present in a particular location, such as wireless networking signals, RFID signals, cellular signals, beacons, etc.

The action 702 may further comprise accessing a directory to identify mobile devices that are associated respectively with each of the scheduled participants. Email directories, corporate directories, or other online directories may be used for this purpose.

An action 704 comprises determining which mobile devices of the scheduled participants are at a scheduled or desired meeting location during the scheduled time of the meeting, and, based on that, which of the scheduled participants are at the meeting location during the scheduled time. The action 704 may be performed by an application running on a mobile device of the participant, such as by the meeting application 206 of FIG. 2. Alternatively, the action 704 may be performed by a server or service, in response to position information received from the mobile devices of the meeting participants.

The action 704 may comprise receiving, retrieving, and/or generating position information indicating (a) locations of mobile devices of scheduled meeting participants relative to the meeting location, (b) locations of the mobile devices relative to each other, and/or (c) information from which such locations can be derived or inferred. This position information may be obtained directly from the mobile devices such as by exchanging communications, information, or signals between the devices. Alternatively, the position information may be gathered indirectly through various types of coordinating devices or services, including web services.

Position information may indicate proximity of the mobile devices to each other or to a common location or reference point. Position information may also, or alternatively, indicate geographic coordinates of the mobile devices. Proximity to a meeting location may be evaluated with reference to a predefined meeting location specified by a calendar, to a meeting location defined by manual check-in at a particular location by one or more of the participants, or to a meeting location defined by a common location at which a plurality of the scheduled participants are present.

More specifically, determining whether a participant is at a particular location may in some cases be performed by comparing the position of the mobile device of the participant with a known location of a meeting. For example, the meeting location may be specified by the calendar in terms of geographic coordinates, and the action 704 may comprise determining whether the mobile device of the participant is at or near those coordinates.

In other cases, especially where the geographic coordinates of the meeting are not available, the action 704 may be performed in response to an explicit act by the participant, such as by the participant manually "checking in" to the meeting. For example, upon arriving at a meeting location, the participant may use the meeting application 206 to indicate that he or she has arrived at the meeting location. The act of checking in may also define the location of the meeting for remaining participants. In other words, the other participants may be considered present at the meeting if they are at the same location as a user who has checked in to the meeting.

In yet other cases, determining which of the scheduled participants are at a meeting location may comprise determining which of the mobile devices are in proximity to each other or are at a common location along with other scheduled participants.

If the participant is not at a meeting location during the scheduled time of the meeting, the actions 702 and 704 are repeated. If the participant is at the meeting location during the scheduled time of the meeting, the method 700 continues with an action 706.

The action 706 comprises creating a meeting or attendance report that lists those of the scheduled meeting participants who are actually present at the meeting. In some cases, the action 706 may comprise simply listing the names of those scheduled participants who are at the meeting, based upon the presence of their mobile devices at the meeting location.

In some embodiments, the action 706 may comprise additional actions that are performed with respect to participants who have been found to be at the meeting location, in order to generate a two-dimensional map of an area that indicates relative positions of the attending participants. The additional actions may include an action 708 of determining relative positions of the attending participants. This may be performed by receiving or deriving position information regarding mobile devices of those participants who are present at the meeting location. As discussed above, the position information may comprise geographic coordinates. Alternatively, various local sensors and communications techniques may be used to determine positions of mobile devices relative to each other, including the use of device compasses, gyroscopes, accelerometers, global positioning devices, facial recognition techniques, and so forth. The various mobile devices may communicate directly with each other to exchange information from which relative positions can be derived, or may communicate with or through central services. Similarly, the mobile devices themselves may process the position information to determine relative positions, or the information may be analyzed by central services.

An action 710 comprises generating a graphical attendance map or seating map that indicates positions of the attending meeting participants. Participant positions may be shown graphically, such as by generating a two-dimensional map of an area that includes the locations of the participants, or by showing a still image or live image of the attending meeting participants, annotated to indicate the names of the attending meeting participants. The attendance report may be displayed on the mobile device of any one or more of the meeting participants, and/or on other types of displays, including displays that may be viewed by other individuals.

The actions 706, 708, and 710 are performed repetitively during the scheduled time of the meeting, to report in real time those of the scheduled meeting participants who are at the location of the meeting. In certain embodiments, the meeting report may also list those who are absent from the meeting.

An action 712, performed at the conclusion of the meeting, may comprise recording or archiving meeting reports generated in the action 706. Archived meeting reports may be referenced as historical records. In addition, archived meeting reports may be used as the basis for generating communications to individual meeting participants, either during the meeting or subsequent to the meeting. For example, meeting notes may be sent to meeting participants based on archived meeting reports.

FIG. 8 illustrates relevant components of a device or system 800 that may be used to implement the functionality described herein. The device or system 800 may comprise a computerized device having network or other communications capabilities. For example, the device or system 800 may comprise a personal computer, a tablet computer, a smartphone, a media consumption device, a gaming device, or any other type of device that is capable of generating a graphical user interface.

In a very basic configuration, an example device 800 may comprise a processing unit composed of one or more processors 802, and memory 804. Depending on the configuration of the device or system 800, the memory 802 may be a type of computer storage media and may include volatile and nonvolatile memory. Thus, the memory 802 may include, but is not limited to, RAM, ROM, EEPROM, flash memory, or other memory technology.

The memory 802 may be used to store any number of executable components 806 that are executable by the processing unit 802. In many embodiments, these executable components comprise instructions or programs that are executable by the processor(s) 802, and that when executed implement operational logic for performing the actions and functions described above.

Executable components stored in the memory 804 may include the functional elements illustrated in FIG. 2, such as the meeting application 206, the calendar component 208, the user directory component 210, and the social network component 212, as well as an operating system, communications components, user interface components, etc.

Physical components of the device or system 800 may include the communications components 214, the location detection components 214, and various types of sensors 808 such as compasses, gyroscopes, accelerometers, cameras, microphones, and so forth. The device or system 800 may include many other elements and components that are not shown.

Although the subject matter has been described in language specific to structural features, it is to be understood that the subject matter defined in the appended claims is not necessarily limited to the specific features described. Rather, the specific features are disclosed as illustrative forms of implementing the claims.

What is claimed is:

1. A mobile device, comprising:
   a graphical display;
   a camera;
   one or more processors; and
   one or more computer-readable media storing computer-executable instructions that, when executed by the one or more processors, cause the one or more processors to perform acts comprising:
   during a time of a meeting, receiving first position information of a first mobile device, the first mobile device corresponding to a first participant of the meeting;
   during the time of the meeting, receiving second position information of a second mobile device, the second mobile device corresponding to a second participant of the meeting;
   presenting a first element representing the first participant on the graphical display based at least in part on the received first position information;
   presenting a second element representing the second participant on the graphical display based at least in part on the received second position information;
   capturing, via the camera, an image of the first participant;
   displaying the image on the graphical display; and
   annotating the image with information corresponding to the first participant.

2. The mobile device of claim 1, wherein the acts further comprise:
   determining a time of the meeting; and
   identifying a plurality of scheduled participants of the meeting, the plurality of scheduled participants including the first participant and the second participant.

3. The mobile device of claim 1, wherein the first position information comprises first geographic coordinates of the first mobile device and the second position information comprises second geographic coordinates of the second mobile device.

4. The mobile device of claim 1, the acts further comprising displaying a map on the graphical display, wherein the map illustrates relative positions of the first mobile device and the second mobile device during the meeting.

5. The mobile device of claim 1, the acts further comprising archiving information regarding meeting attendance based at least in part on the presenting.

6. The mobile device of claim 1, the acts further comprising:
   accessing a calendar to determine a time of the meeting;
   determining, based at least in part on the calendar, that the first participant and the second participant are scheduled to attend the meeting; and
   determining that the first participant is associated with the first mobile device and that the second participant is associated with the second mobile device.

7. The mobile device of claim 1, the acts further comprising:
   identifying a scheduled location of the meeting;
   determining that the first participant is attending the meeting by determining that the first mobile device is at the scheduled location of the meeting; and
   determining that the second participant is attending the meeting by determining that the second mobile device is at the scheduled location of the meeting.

8. A method, comprising:
   receiving first position information of a first mobile device, the first mobile device corresponding to a first participant of a meeting;
   receiving second position information of a second mobile device, the second mobile device corresponding to a second participant of the meeting;
   presenting a first element representing the first participant on a graphical display based at least in part on the received first position information;

presenting a second element representing the second participant on the graphical display based at least in part on the received second position information;
capturing, via a camera, an image of the first participant;
displaying the image on the graphical display; and
annotating the image with information corresponding to the first participant.

9. The method of claim 8, further comprising:
displaying a map on the graphical display, wherein the map illustrates relative positions of the first mobile device and the second mobile device.

10. The method of claim 8, further comprising:
accessing a calendar to determine a time of the meeting;
determining, based at least in part on the calendar, that the first participant and the second participant are scheduled to attend the meeting; and
determining that the first participant is associated with the first mobile device and that the second participant is associated with the second mobile device.

11. The method of claim 8, the acts further comprising:
identifying a scheduled location of the meeting;
determining that the first participant is attending the meeting by determining that the first mobile device is at the scheduled location of the meeting; and
determining that the second participant is attending the meeting by determining that the second mobile device is at the scheduled location of the meeting.

12. The method of claim 11, further comprising:
determining, based at least in part on the calendar, a third participant is scheduled to attend the meeting;
determining that the third participant is associated with a third mobile device;
determining that the third participant is not attending the meeting by determining that the third mobile device is not at the scheduled location of the meeting; and
displaying on the graphical display that the third participant is not attending the meeting.

13. The method of claim 8, further comprising:
detecting a selection of the first participant from the graphical display; and
enabling reproduction of video captured from a camera of the first mobile device.

14. One or more non-transitory computer-readable media storing computer-executable instructions that, when executed by one or more processors, cause the one or more processors to perform acts comprising:
determining a plurality of scheduled participants who are scheduled to attend a meeting;
identifying individual mobile devices of a plurality of mobile devices that are associated respectively with individual participants of the scheduled participants;
during the time of the meeting, receiving first position information regarding a first mobile device of the plurality of the mobile devices;
determining that a first participant corresponding to the first mobile device is attending the meeting based at least in part on the first position information;
generating an attendance map based at least in part on the position information, the attendance map indicating the name of the first participant;
receiving an image of the first participant; and
causing display of the attendance map with the image on a graphical display.

15. The or more non-transitory computer-readable media of claim 14, wherein the computer-executable instructions, when executed by one or more processors, further cause the one or more processors to perform acts comprising:
receiving, via the attendance map, a selection of the first participant;
receiving spoken audio captured from a microphone of the first mobile device of the first participant of the scheduled participants; and
sending the spoken audio to at least a subset of the plurality mobile devices corresponding to the scheduled participants present at the meeting.

16. The one or more non-transitory computer-readable media of claim 14, wherein the first position information comprises geographic coordinates of the first mobile devices.

17. The one or more non-transitory computer-readable media of claim 14, wherein the first position information indicates proximity of the first mobile devices to another one of the plurality of mobile devices.

18. The or more non-transitory computer-readable media of claim 14, wherein the computer-executable instructions, when executed by one or more processors, further cause the one or more processors to perform acts comprising:
annotating the attendance map with information corresponding to the first participant.

19. The or more non-transitory computer-readable media of claim 14, wherein the computer-executable instructions, when executed by one or more processors, further cause the one or more processors to perform acts comprising:
identifying a scheduled location of the meeting; and
identifying a subset of the mobile devices that are at the meeting by determining which of the plurality of mobile devices associated with the plurality of scheduled participants are at the scheduled location of the meeting.

20. The or more non-transitory computer-readable media of claim 14, wherein the computer-executable instructions, when executed by one or more processors, further cause the one or more processors to perform acts comprising:
accessing a social network to obtain information regarding the first participant of the plurality of participants that is at the meeting, wherein the attendance map indicates at least some of the obtained information.

* * * * *